(12) United States Patent
Fujino

(10) Patent No.: US 7,056,454 B2
(45) Date of Patent: Jun. 6, 2006

(54) ION GENERATOR AND ITS MANUFACTURING METHOD

(76) Inventor: Tomozo Fujino, 3-29-10 Ebisu, Shibuya-Ko, Tokyo (JP)

( * ) Notice: Subject to any disclaimer, the term of this patent is extended or adjusted under 35 U.S.C. 154(b) by 440 days.

(21) Appl. No.: 10/283,515

(22) Filed: Oct. 30, 2002

(65) Prior Publication Data

US 2003/0098420 A1 May 29, 2003

(30) Foreign Application Priority Data

Nov. 26, 2001 (JP) .............................. 2001-358963

(51) Int. Cl.
*H01B 1/06* (2006.01)
(52) U.S. Cl. .............................. 252/520.2; 252/520.22; 501/134; 501/138
(58) Field of Classification Search ............. 252/520.2, 252/520.22; 250/423 R; 501/86, 134, 138 501/139; 106/286.4
See application file for complete search history.

(56) References Cited

U.S. PATENT DOCUMENTS

| | | | |
|---|---|---|---|
| 4,529,410 A | 7/1985 | Khaladji et al. | 51/309 |
| 5,468,427 A | 11/1995 | Stangle et al. | 264/3.4 |
| 5,660,773 A | 8/1997 | Stangle et al. | 264/6 |
| 5,683,953 A | 11/1997 | Mills | 502/405 |
| 5,866,092 A | 2/1999 | Fukuda et al. | 423/263 |
| 5,872,072 A | 2/1999 | Mouri et al. | 502/208 |
| 5,897,784 A | 4/1999 | Mills | 210/705 |
| 6,030,449 A | 2/2000 | Fukuda et al. | 117/13 |
| 6,150,299 A | 11/2000 | Umemoto et al. | 502/304 |
| 6,179,971 B1 | 1/2001 | Kittrell et al. | 204/158.2 |
| 6,294,006 B1 * | 9/2001 | Andou | 106/14.05 |
| 6,312,604 B1 | 11/2001 | Denkewicz, Jr. et al. | 210/728 |
| 6,338,840 B1 | 1/2002 | Allan et al. | 424/65 |
| 6,649,090 B1 * | 11/2003 | Funaki et al. | 252/500 |
| 2001/0041169 A1 | 11/2001 | Allan et al. | 424/65 |

FOREIGN PATENT DOCUMENTS

| | | | |
|---|---|---|---|
| EP | 0037224 | | 3/1981 |
| EP | 1132445 | * | 9/2001 |
| JP | 03218963 | * | 9/1991 |
| JP | 07061898 | * | 3/1995 |
| JP | 07088370 A | | 4/1995 |
| JP | 08089799 A | | 4/1996 |
| JP | 08281070 A | | 10/1996 |
| JP | 10-168361 | * | 6/1998 |
| JP | 1010174881 A | | 6/1998 |
| JP | 2001-131529 | * | 5/2001 |
| JP | 2001-218853 | * | 8/2001 |
| JP | 2002-020164 | * | 1/2002 |

OTHER PUBLICATIONS

Haneda et al (Magnetic Properties of Small Particles . . . , IEEE Transactions on Magnetics 35, 5, Sep. 1999, 3490-95.*

* cited by examiner

*Primary Examiner*—Mark Kopec
(74) *Attorney, Agent, or Firm*—Seth Natter; Natter & Natter

(57) ABSTRACT

An ion generator with increased generation of negative ions and its method of manufacture are disclosed. For an ion generator of the present invention, a titanium oxide powder is added to an ion generator that generates negative ions.

10 Claims, 1 Drawing Sheet

ION GENERATOR AND ITS MANUFACTURING METHOD

BACKGROUND OF THE INVENTION

1. Industrial Field of Utilization

This invention pertains to an ion generator that generates negative ions and its manufacturing method.

2. Prior Art

Previously, various items are known as ion generators that generate negative ions.

However, prior ion generators simply cannot obtain any effect of generating negative ions.

SUMMARY OF THE INVENTION

This invention has the objective of offering an ion generator and its manufacturing method that realizes various effects by increasing the generation of negative ions.

In order to realize the above-mentioned objective, the invention as described is characterized by adding a titanium oxide powder or a titanium oxide liquid to an ion generator that generates negative ions.

Further, the invention as described is characterized by mixing an ion generator that generates negative ions and a titanium oxide powder or titanium oxide liquid in a ratio of 1:99 through 99:1 by weight for an ion generator.

Further, the invention as described is characterized by forming an ion generator that generates negative ions by mixing a material that contains a rare earth element and a polar material with spontaneous polarization for an ion generator.

Further, the invention as described is characterized by forming an ion generator that generates negative ions by mixing a baked material that contains a rare earth element and a polar material with spontaneous polarization.

Further, the invention as described is characterized by utilization of a precious or semi-precious stone for a polar material with spontaneous polarization for an ion generator.

Further, the invention as described is characterized by the utilization of a garnet as a precious or semi-precious stone for an ion generator.

Further, the invention as described is characterized by adding titanium oxide powder or titanium oxide liquid for an ion generator that generates negative ions.

Further, the invention as described is characterized by mixing an ion generator that generates negative ions and titanium oxide powder or titanium oxide liquid in a ratio of 1:99 through 99:1 by weight in a manufacturing method of an ion generator.

EXPLANATION OF THE SYMBOLS

The numeral 1 denotes an ion generator that generates negative ions.

The numeral 2 denotes titanium oxide powder and the numeral 3 denotes titanium oxide liquid.

PREFERRED EMBODIMENTS OF THE INVENTION

Figure 1:
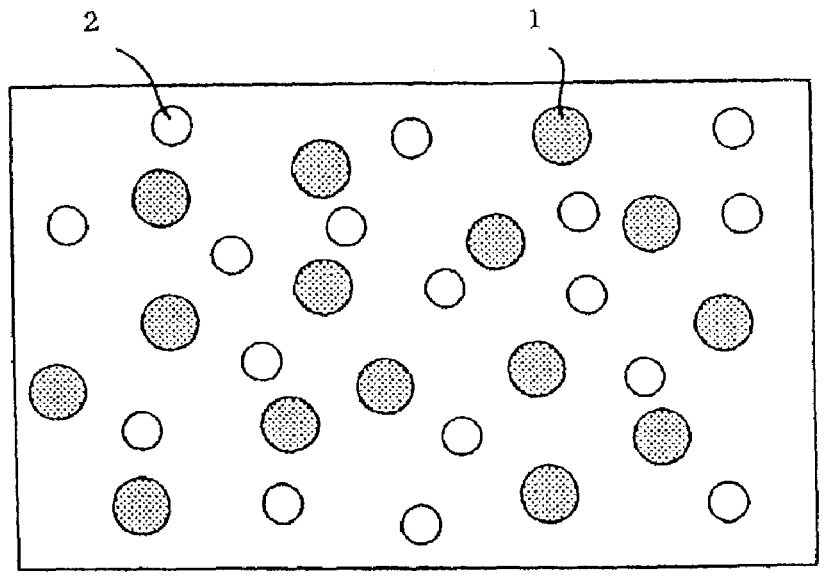
FIG. 1 shows one example of an ion generator of the present invention.

FIG. 1 is a figure that shows a 1st construction of an ion generator of the present invention. When referring to FIG. 1, the ion generator of the 1st construction example of this invention is one with a titanium oxide powder 2 added to an ion generator 1 that generates negative ions.

Figure 2:
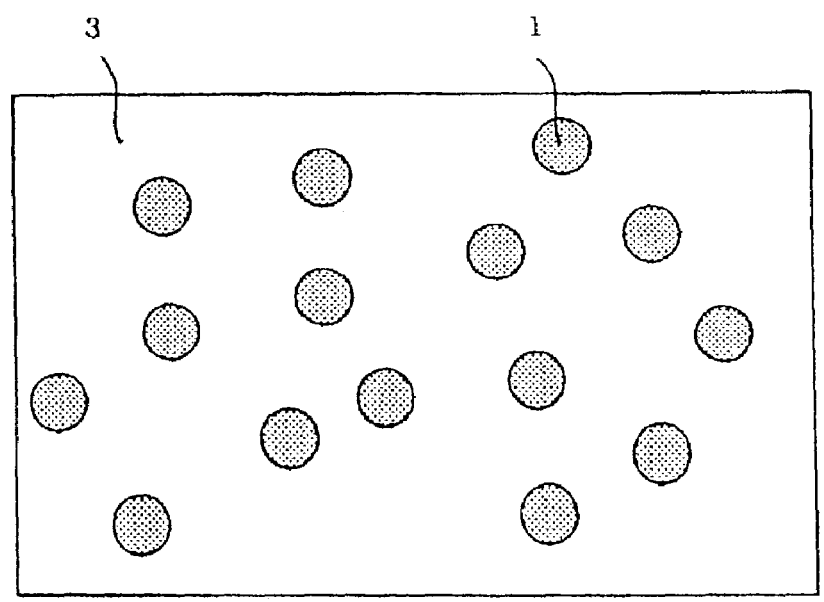
FIG. 2 shows another example of an ion generator of the present invention.

Further, FIG. 2 is a figure that shows a 2nd construction example of an ion generator of the present invention. When referring to FIG. 2, an ion generator of the 2nd construction example of the present invention is one with a titanium oxide liquid 3 added to an ion generator 1 that generates negative ions.

Here, the ion generator 1 that generates negative ions and the titanium oxide powder 2 or titanium oxide liquid 3 are mixed in a ratio of 1:99 through 99:1 by weight for ion generators of the above-mentioned 1st or 2nd construction examples.

The present invention increases the effect of generating negative ions, and an effect of nitrogen oxides ($NO_x$) being decomposed and an effect of increasing the deodorizing power can be further given by adding titanium oxide powder 2 or titanium oxide liquid 3 to an ion generator 1 that generates negative ions.

Also, by mixing the ion generator 1 that generates negative ions and the titanium oxide powder 2 or titanium oxide liquid 3 in a ratio of 1:99 through 99:1 by weight, a photocatalytic effect can be realized even without any light. Further, an effect appears such as having a photocatalyst by increasing the prior [art] negative ion effects.

Therefore, an ion generator of the above-mentioned 1st or 2nd construction example (an ion generator of the present invention) can be utilized for a variety of applications. For example, an ion generator (powder) of the present invention can be included in a synthetic resin and a synthetic resin that contains an ion generator of the present invention can be manufactured as a negative ion generating fiber, master patch and nonwoven fabric. This kind of fiber, master patch and unwoven material, for example, can be applied to fields like clothing, filters, trim, bedding, textiles, form finished products, business machines, sanitary materials, automobiles, residential related products and H.V.A.C. [heating, ventilating & air conditioning] equipment.

Further, an ion generator (powder) of the present invention can be contained in inorganic (ceramic) or organic paints; paints that contain an ion generator of the present invention can be manufactured as things like negative ion generating construction materials, clean rooms and air purification products. These kinds of construction materials, clean rooms and air purification products can be applied in fields like, for example, residential related products, office machines, sanitary porcelain, textiles, architectural materials, various finished goods and H.V.A.C. [heating, ventilating & air conditioning] related materials.

Also, an ion generator (powder) of the present invention can be contained in things like balls and plates and balls; and, plates that contain ion generators of the present invention, for example, can be manufactured into things like negative ion generating exhaust gas treating products, air purification products, sanitary materials and water treatment products. Concretely, [these] can be applied to things like deodorizing products, water treatment products, bedding, H.V.A.C. [heating, ventilating & air conditioning] products and textiles.

Further, an ion generator (powder) of the present invention can be contained in paper and paper that contains an ion generator of the present invention can be manufactured as things like construction materials (for example, trim) that generate negative ions.

Also, an ion generator 1 that generates negative ions can be made, for example, by mixing a material that contains a rare earth element and a polar material with spontaneous polarization.

Thus, concretely, an ion generator 1 that generates negative ions can be made by mixing a baked material that contains a rare earth element and a polar material with spontaneous polarization.

Thus, concretely, an ion generator 1 that generates negative ions, can be made by mixing a pulverized material that contains a rare earth element baked at temperatures to an extent of, for example, 1000.degree. C. to 1800.degree. C., and a pulverized polar material with spontaneous polarization.

Here, as the mixing ratio of the material that contains a rare earth element (further, this is baked and pulverized) and a polar material with spontaneous polarization, the polar material with spontaneous polarization is mixed into the material which contains a rare earth element at an extent of 5 to 50 weight %.

Further, for example, a mixed rare earth element can be used as a material that contains a rare earth element. For example, things like natural minerals like bastnasite, xenotime, monazite, monazite mixtures or mixtures of these can be used.

Further, ones like precious or semiprecious stones, like garnets and orthosilicate, can be used as polar materials with spontaneous polarization.

Thus, concretely, the use of garnets as the precious or semiprecious stones for polar material with spontaneous polarization is desirable.

Ion generators made such as this can offer this in, for example, a powder form.

An above-mentioned ion generator 1 that generates negative ions can be made by manufacturing methods such as the following, concretely. Further, after baking a material that contains a rare earth element (for example, ones like the above-mentioned natural minerals) at 1000.degree. C. to 1800.degree. C., this [material] is pulverized to a size of the extent of 3–5 microns, for example.

The polar material with spontaneous polarization (for example, garnet) is also pulverized to a size of the extent of 3–5 microns.

In this way, an ion generator 1 that generates negative ions can be made by mixing a pulverized polar material (a polar material with spontaneous polarization) into a pulverized material that contains a rare earth (baked pulverized material) at a ratio of an extent of 5 to 50 weight %.

In an ion generator 1 that generates a negative ion which is made in this way, electrical properties of the polar material with spontaneous polarization, that is, negative ions that are generated from the polar material have an effect of the negative ions (enriched durability) continuing for a long period by being brought out as a natural form due to a material that contains a rare earth element (this functions as one type of stimulant). Thus, for an above-mentioned ion generator 1 that generates negative ions, adequate negative ions continue being generated for a long period even only by being left as it is at room temperature without requiring an energy source such as electricity (having enriched durability with the negative ion generating action continuing over a long period).

Thus, only materials that can be simply procured which exist in the natural world of materials that contain rare earth elements (like natural minerals) and polar materials with spontaneous polarization (like precious and semiprecious stones such as garnets) are used as raw materials for an aforementioned ion generator which generates negative ions and [this] can be made as a natural inorganic substance.

Further, an ion generator 1 that generates negative ions can be offered at low cost without requiring the use of things like, for example, unique equipment when making an above-mentioned ion generator that generates negative ions.

The above-mentioned ion generator 1 which generates negative ions has effects such as the following due to generation of adequate negative ions continuing for a long period.

Thus, an above-mentioned ion generator 1 that generates negative ions has antibacterial effects and, further, can decompose harmful components and odor molecules. Further, [this] can temper stress by improving circulation and metabolism by activating biological properties by increasing the negative ions in the vicinity of the body surface. Further, static electricity is decreased by the negative ions and things like dirt and dust have a difficult time collecting.

EFFECTS OF THE INVENTION

As explained above, when done according to the invention as described an effect of decomposing nitrogen oxides (NO.sub.x), an effect of increasing the deodorizing power and an effect of attaining antibacterial properties can be realized by increasing the effect of generating negative ions since titanium oxide powder or titanium oxide liquid is added to an ion generator that generates negative ions.

In particular, when done according to the invention as described an ion generator that generates negative ions and a titanium oxide powder or titanium oxide liquid are mixed in a ratio of 1:99 to 99:1 by weight, thus a photocatalytic effect can be realized even without any light. Thus, an effect of having a photocatalyst can be realized in addition to the prior [art] negative ion effects.

Further, when done according to the invention as described concretely, an ion generator that generates negative ions that enrich the durability can be offered at low cost with a material that can be easily procured which exists in the natural world as a raw material since an ion generator that generates negative ions is formed by mixing a material that contains a rare earth element and a polar material with spontaneous polarization.

What is claimed is:

1. A method of preparing an ion generator comprising:
   a) baking a material having a rare earth element;
   b) pulverizing the material baked in step a);
   c) pulverizing a polar material capable of spontaneous polarization; and
   d) mixing the pulverized material of step b) with the pulverized material of step c).

2. A method of preparing an ion generator in accordance with claim 1 further including:
   e) admixing the mixture of step d) with titanium oxide.

3. A method of preparing an ion generator in accordance with claim 2 wherein the titanium oxide is added in a ratio of 1:99 to 99:1 by weight.

4. A method of preparing an ion generator in accordance with claim 1 wherein step b) includes pulverizing to a particle size of 3–5 microns.

5. A method of preparing an ion generator in accordance with claim 4 wherein step c) includes pulverizing to a particle size of 3–5 microns.

6. A method of preparing an ion generator in accordance with claim 1 wherein step c) includes pulverizing to a particle size of 3–5 microns.

7. A method of preparing an ion generator in accordance with claim 1 wherein step a) includes heating the material to a temperature ranging between 1000° C. and 1800° C.

8. A method of preparing an ion generator in accordance with claim 1 further including the step of selecting the material having a rare earth element from the group consisting of bastnasite, xenotime and monazite.

9. A method of preparing an ion generator in accordance with claim 1 further including the step of selecting the polar material from a group consisting of precious and semiprecious stones.

10. A method of preparing an ion generator in accordance with claim 9 wherein step c) is performed by pulverizing garnet.

* * * * *